United States Patent
Prummer

(10) Patent No.: US 9,945,834 B2
(45) Date of Patent: Apr. 17, 2018

(54) METHOD FOR EXAMINING A PLURALITY OF CULTURED CELLS FOR THE PRESENCE OF PERIODIC STRUCTURES OF AT LEAST ONE TARGET COMPONENT CONTAINED IN THE CULTURED CELLS

(71) Applicant: Hoffmann-La Roche Inc., Nutley, NJ (US)

(72) Inventor: Michael Prummer, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 163 days.

(21) Appl. No.: 15/034,023

(22) PCT Filed: Nov. 5, 2014

(86) PCT No.: PCT/EP2014/073757
§ 371 (c)(1),
(2) Date: May 3, 2016

(87) PCT Pub. No.: WO2015/067628
PCT Pub. Date: May 14, 2015

(65) Prior Publication Data
US 2016/0282324 A1 Sep. 29, 2016

(30) Foreign Application Priority Data
Nov. 6, 2013 (EP) .................................... 13191778

(51) Int. Cl.
*G06T 7/00* (2017.01)
*G01N 33/483* (2006.01)
(Continued)

(52) U.S. Cl.
CPC ..... *G01N 33/4833* (2013.01); *G01N 15/1468* (2013.01); *G01N 33/5038* (2013.01);
(Continued)

(58) Field of Classification Search
None
See application file for complete search history.

(56) References Cited

U.S. PATENT DOCUMENTS

2002/0022716 A1   2/2002   Hartman et al.

FOREIGN PATENT DOCUMENTS

JP    2006296282 A    11/2006
WO    WO-00/66985 A1    11/2000

OTHER PUBLICATIONS

International Search Report Issued in PCT/EP2014/073757 dated Jan. 26, 2015.
(Continued)

*Primary Examiner* — Kim Vu
*Assistant Examiner* — Molly Delaney
(74) *Attorney, Agent, or Firm* — Mintz Levin Cohn Ferris Glovsky and Popeo, P.C.

(57) ABSTRACT

A method for examining cultured cells for the presence of periodic structures comprises the steps of providing cultured cells, fixing the cultured cells, staining the fixed cultured cells using a first staining agent, stimulating the first staining agent causing it to emit light taking a two-dimensional image of the fixed cultured cells, cross-correlating first and second filtered images derived from the image of the fixed cultured cells to obtain a correlation image, and determining the presence or absence of periodic structures in the fixed cultured cells by determining whether there are periodic structures of maxima and minima in brightness in the correlation image.

11 Claims, 4 Drawing Sheets

(51) Int. Cl.
*G01N 33/50* (2006.01)
*G01N 15/14* (2006.01)
*G06K 9/00* (2006.01)

(52) U.S. Cl.
CPC ....... *G01N 33/5061* (2013.01); *G06K 9/0014* (2013.01); *G06T 7/0012* (2013.01); *G06T 2207/20056* (2013.01); *G06T 2207/30024* (2013.01)

(56) References Cited

OTHER PUBLICATIONS

Ultra Highspeed et al: "utomated iosystems ore Your High Content Screening Resource Opera QEHS", Apr. 2, 2012, XP055107160, pp. 5, 7-8, 10, 14-15.

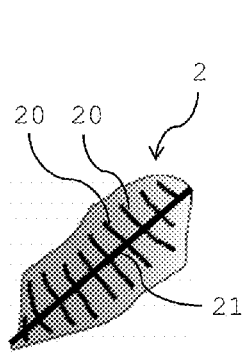 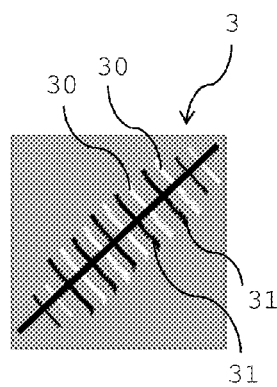 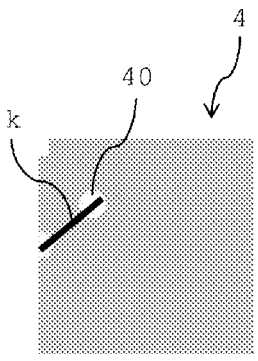
Fig. 3         Fig. 4         Fig. 5
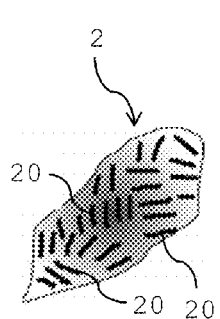 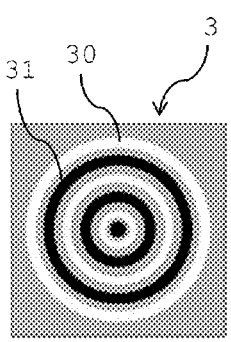 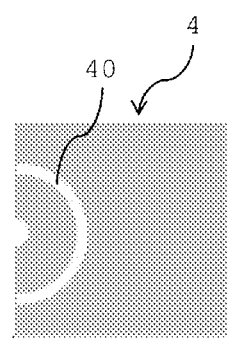
Fig. 6         Fig. 7         Fig. 8
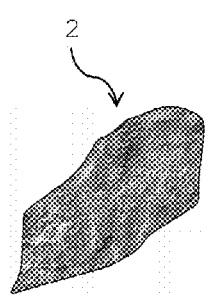 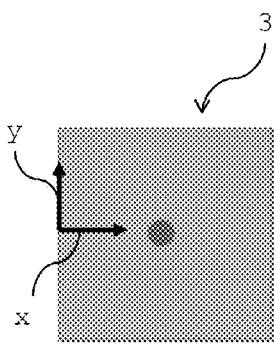 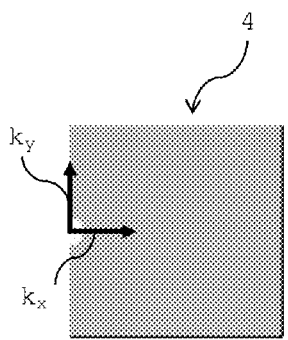
Fig. 9         Fig. 10        Fig. 11

METHOD FOR EXAMINING A PLURALITY OF CULTURED CELLS FOR THE PRESENCE OF PERIODIC STRUCTURES OF AT LEAST ONE TARGET COMPONENT CONTAINED IN THE CULTURED CELLS

CROSS-REFERENCE TO RELATED APPLICATIONS

This application is a national stage application, filed under 35 U.S.C. § 371, of International Application No. PCT/EP2014/073757 filed on Nov. 5, 2014, which claims priority to European Patent Application No. 13191778.3 filed on Nov. 6, 2013, the contents of each of which are hereby fully incorporated by reference.

FIELD OF THE INVENTION

The present invention relates to a method for examining a plurality of cultured cells for the presence of periodic structures of at least one target component (e.g. one or more proteins) contained in the cultured cells.

BACKGROUND

Several phenotypes of severe diseases of the myocardium (or of skeletal muscles) are associated with an impairment of the sarcomere structure in the cardiomyocytes (or myocytes, respectively). For the sake of simplicity, in the following only cardiomyocytes are referred to. In cardiomyocytes, the sarcomere is the smallest subunit which is able to contract and relax.

A sarcomere is schematically shown in FIG. 1 (relaxed state) and FIG. 2 (contracted state). Sarcomere 1 is bounded by two z-disks 10 and further comprises two inter-digitized filament systems. The thin filaments of the first filament system of the two inter-digitized filament systems are composed of hexameric actin strands 11, the thick filaments of the second filament system of the two inter-digitized filament systems are composed of hexameric myosin strands 12. The myosin strands 12 are attached to the two z-disks 10 through two elastic elements 13 composed of protein titin. Upon hydrolysis of ATP (Adenosinetriphosphate), the motor protein myosin of the myosin strands 12 undergoes a conformational change which is converted to a power stroke that shifts the actin strands 11, leading to contraction of the sarcomere 1 (see FIG. 2). Contraction occurring for a large plurality of such sarcomeres 1 leads to contraction of the myocardium, while the reverse process leads to relaxation of the myocardium.

This contractile motion can already be observed in mature cultured living cardiomyocytes which exhibit spontaneous and synchronized beating, and this spontaneous and synchronized beating of the living cardiomyocytes can be used to characterize the mature development state of the living cardiomyocytes.

In fixed cardiomyocytes the structural integrity of the sarcomere structures is indicative of the mature development state of the cardiomyocytes. Fixing the cardiomyocytes may be performed, for example, by adding detergent to the living cardiomyocytes whereby the cell membranes of the living cardiomyocytes get damaged (the living cardiomyocytes are killed) and by adding formaldehyde whereby the proteins contained in the cardiomyocytes are cross-linked, however, the structures of the proteins in the cardiomyocytes are maintained and remain fixed.

For identifying potential drug candidate substances against diseases of the myocardium which are associated with impairment of the sarcomere structures, in vitro experiments are conducted in which the living cardiomyocytes are stressed by adding substances like glucose and/or endothelin until the cardiomyocytes lose their ability to beat without killing the cardiomyocytes (simulation of a cardiomyopathy). Thereafter, a drug candidate substance is added to the stressed cardiomyocytes in order to examine whether or not the drug candidate substance has a recovering effect on the cardiomyocytes, this recovering effect resulting in the cardiomyocytes starting to beat again. For this examination, a small movie of the cardiomyocytes is recorded and is analyzed as to whether the cardiomyocytes have started to beat again (the beating contraction and subsequent relaxation cycles can only be assessed when analyzing a movie). As outlined, however, this analysis of the movies must be performed by a person watching the movies, this being time- and resource-consuming. In addition, the humans watching and analyzing the movies must have the required education and skill.

Alternatively, after the drug candidate substance has been added to the living cardiomyocytes, and after these have been fixed subsequently, the fixed cardiomyocytes are examined for the presence of periodic structures of sarcomeres. Such periodic structures of sarcomeres are indicative of the cardiomyocytes having recovered prior to fixation. This can be performed by taking an image of the fixed cardiomyocytes that must be carefully analyzed by humans through optical inspection. This is again very time- and resource-consuming, and the person performing the optical inspection must have the required education and skill. Even then the images are very difficult to analyze.

SUMMARY OF THE INVENTION

It is therefore an object of the present invention to suggest an improved method for examining cultured cells for the presence of periodic structures of specific components in the cultured cells in general. More particularly, it is an object of the present invention to suggest a method for identifying potential drug candidate substances for the treatment of muscle diseases or myocardium diseases associated with impairment of the sarcomere structures.

According to one aspect, the present invention suggests a method for examining a plurality of cultured cells for the presence of periodic structures of at least one target component contained in the cultured cells. The method comprises the steps of:

providing a plurality of cultured cells to be examined, fixing the cultured cells to be examined while maintaining any structures of at least one target component contained in the cultured cells, staining the at least one target component contained in the fixed cultured cells using a first staining agent binding to the at least one target component and capable of emitting light of a first wavelength upon stimulation, stimulating the first staining agent causing it to emit light of the first wavelength, taking a two-dimensional image of the fixed cultured cells with the first staining agent emitting light of the first wavelength, deriving from this two-dimensional image of the fixed cultured cells a two-dimensional first filtered image showing in bright only those portions containing the at least one target component to which the first staining agent has bound, auto-correlating the first filtered image, or cross-correlating the first filtered image with a two-dimensional second filtered image derived from the two-dimensional image of the fixed cultured cells and showing in bright only those portions other than the ones containing the at least one target component to which the first staining agent has bound, to obtain a two-dimensional correlation image, and determining the presence or absence of periodic structures of the at least one target component contained in the fixed cultured cells by determining whether there are periodic structures of maxima and minima in brightness in the two-dimensional correlation image.

Although in general the method is capable of in vitro examining any type of cells for the presence of any periodic structures in the cells, it is particularly suitable to examine muscles cells and in particular cardiomyocytes for the presence of periodic structures of sarcomeres. Therefore, by way of example in the following it is referred to the examination of cardiomyocytes for the presence of periodic structures of sarcomeres.

Generally, the cultured cardiomyocytes to be examined, for example living cardiomyocytes that have been stressed by adding glucose and/or endothelin (or any other substance suitable) to make the living cardiomyocytes lose their ability to beat (simulation of a cardiomyopathy) and to which subsequently the drug candidate substance has been added, are fixed. Although fixing the cardiomyocytes damages the cell membranes and thus "kills" the cardiomyocytes, any periodic sarcomere structures contained in the cardiomyocytes are maintained through the fixing step. Although the cardio-myocytes to be examined are no longer alive, they are preferably held in a neutral liquid to prevent them from drying out.

At least one component of the sarcomere of the fixed cardiomyocytes, for example the protein Actinin contained in the z-disks of the sarcomeres of the fixed cardiomyocytes, is then stained. For that purpose, a suitable staining agent may be added to the fixed cardiomyocytes. An example for such suitable staining agent may be an Actinin antibody provided with a label which is capable of emitting light of a predetermined wavelength upon stimulation. Once the Actinin antibody provided with the label has bound to the protein Actinin contained in the cardiomyocytes the staining agent is stimulated causing the label to emit light of the predetermined wavelength.

During emission of the light of the predetermined wavelength, a two-dimensional image of the cultured cardiomyocytes is taken. From this two-dimensional image of the fixed cultured cardiomyocytes a two-dimensional first filtered image is derived. This first filtered image shows in bright only those portions of the image of the fixed cultured cardiomyocytes which contain the protein Actinin to which the Actinin antibody with the label has bound.

Generally, there are two options then. The first option is to auto-correlate the first filtered image to generate a two-dimensional correlation image. The second option is to cross-correlate the first filtered image with a second filtered image. The second filtered image also is a two-dimensional image derived from the two-dimensional image of the fixed cultured cardiomyocytes. However, in contrast to the first filtered image the second filtered image shows in bright only those portions of the fixed cultured cardiomyocytes other than the ones of the stained protein Actinin. The first and second filtered images are then cross-correlated to generate a two-dimensional correlation image.

In mathematical terms the auto-correlation of the first filtered image corresponds to a convolution of the intensities of the individual pixels of the first filtered image with the intensities of the individual pixels of the first filtered image, or to say it in other words the auto-correlation is a convolution of the first filtered image with itself. The cross-correlation of the first filtered image and the second filtered images corresponds to a convolution of the intensities in brightness of the individual pixels of the first and second filtered images (which are anti-correlated by definition at zero spatial shift). However, having a computer perform a mathematical convolution of the intensities in brightness of the individual pixels would result in a very high computational effort. Although this is possible in principle, there are more efficient ways than performing the mathematical convolution, and these more efficient ways come to the same result but require much less computational effort. Examples for such more efficient ways are discussed below in more detail.

In case the correlation image shows periodic structures in the maxima and minima in brightness this means, that there are periodic structures of the protein Actinin contained in the z-disks of the sarcomeres of the fixed cardiomyocytes. Depending on how the periodic structures in the correlation image look like it is possible to draw conclusions from the correlation image on the periodic sarcomere structures contained in the cardiomyocytes, as will be explained in more detail below with the aid of specific examples.

Overall, the method according to the invention provides an improved in vitro method (for example, it can be carried out in the wells of standard micro-plates) for examining cultured cells for the presence of periodic structures contained in the cultured cells which does no longer require essential and time- and resource consuming steps of prior art methods (recording of movies, optical analysis of the movies and determination whether or not the cardiomyocytes are beating; complicated optical analysis of fixed cultured cells, if possible at all). Instead, the method according to the invention suggests taking the above-described two-dimensional image of the fixed cultured cells, deriving the filtered image or filtered images from this two-dimensional image of the fixed cultured cells, correlating these filtered images to generate a correlation image, and determining the presence or absence of periodic structures in the cultured cells by determining whether there are periodic structures of maxima and minima in brightness in the correlation image. These steps can be performed in a fully automated manner.

In some embodiments of the method according to the invention, the step of deriving the two-dimensional first and second filtered images comprises performing a ridge-valley filtering of the two-dimensional image of the fixed cultured cells to generate a two-dimensional ridge image and to generate a valley image. In the ridge image stripe-shaped structures of the at least one target component to which the first staining agent has bound are enhanced in brightness and structures other than stripe-shaped structures of the at least one target component to which the first staining agent has bound are attenuated in brightness. The ridge image forms the first filtered image. In the valley image stripe-shaped structures arranged between the stripe-shaped structures of the target component to which the first staining agent has bound are enhanced in brightness and structures other than stripe-shaped structures arranged between the stripe-shaped structures to which the first staining agent has bound are attenuated in brightness. This valley image forms the second filtered image. The ridge image and the valley image are then cross-correlated to form the correlation image.

This embodiment of the method according to the invention is advantageous for the detection of stripe-shaped structures such as sarcomere structures in cardiomyocytes, since the ridge-valley filtering enhances only stripe-shaped structures while attenuating any structures other than stripe-shaped structures. Accordingly, structures other than stripe-shaped structures contained in the image of the fixed cultured cells are suppressed. For the afore-described example related to the stained protein Actinin contained in the z-disks of the sarcomeres of the cardiomyocytes (assuming that the fixed cardiomyocytes contain sarcomere structures which are intact) this means, that the ridge image enhances in brightness only the structures of the stained Actinin protein (z-disks) while any other stripe-shaped information contained in the image of the cultured cells is suppressed in the ridge image (these pixels are dark in the ridge image). This information is contained, however, in the valley image which enhances stripe-shaped structures between the stripe-shaped structures of the stained Actinin protein. In order to use this information, too, when generating the correlation image, the ridge image is cross-correlated with the valley image to generate the correlation image. In general, however, it would also be conceivable to only auto-correlate the ridge image to generate the correlation image. However, in this case the information suppressed in the ridge image is lost and is no longer contained in the correlation image. Therefore, the cross-correlation of the ridge image and the valley image is advantageous over the auto-correlation of the ridge image.

In some further embodiments of the method according to the invention, the correlation image is generated by:
  performing a Fourier transformation of the first filtered image to obtain a two-dimensional Fourier transformed first filtered image and multiplying the Fourier transformed image with itself to obtain a two-dimensional Fourier transformed correlation image, or
  performing a Fourier transformation of the first filtered image to obtain a two-dimensional Fourier transformed first filtered image and performing a Fourier transformation of the second filtered image to obtain a two-dimensional Fourier transformed second filtered image and multiplying the Fourier transformed first filtered image and the Fourier transformed second filtered image to obtain a two-dimensional multiplied Fourier transformed correlation image,
  performing an inverse Fourier transformation of the multiplied Fourier transformed correlation image to obtain the two-dimensional correlation image.

This embodiment is advantageous in that it greatly reduces the computational effort for obtaining the correlation image, either through auto-correlation of the first filtered image or through cross-correlation of the first filtered image and the second filtered image. As has been discussed above, auto-correlation or cross-correlation in mathematical terms stands for a convolution to be performed. In order to illustrate this very significant reduction of the computational effort in obtaining the correlation image, an example will be discussed in the following.

Assuming that a two-dimensional image of the cultured cells has been taken, and that the ridge image and the valley image has been derived therefrom. Let $$\delta I_r(x,y) = I_r(x,y) - \bar{I}_r \text{ and}$$

$$\delta I_v(x,y) = I_v(x,y) - \bar{I}_v$$

represent the differential ridge and valley images, with
$I_r(x,y)$ Intensity of the ridge image at coordinate x,y
$\bar{I}_r$ Average intensity (brightness) of the ridge image
$I_v(x,y)$ Intensity of the valley image at coordinate x,y
$\bar{I}_v$ Average intensity (brightness) of the valley image.

The correlation image then is represented by $$CCI(dx, dy) = \frac{1}{N_{pixels}} \sum_{x,y} \delta I_r(x, y) \cdot \delta I_v(x + dx, y + dy)$$

This means that for obtaining an intensity value of the correlation image for one specific relative shift (dx,dy) of the ridge and valley images, the intensity value (brightness) for that specific shift (dx,dy) must be calculated in accordance with the equation outlined above (convolution). Accordingly, for obtaining the intensity values in the correlation image for all relative shifts (dx,dy) there is much computational work to be done using the ridge and valley images. However, this computational work is very significantly reduced after Fourier transformation of the ridge and valley images. The convolution of the ridge and valley images outlined above corresponds to one single multiplication of the Fourier transformed ridge and valley images (with no relative shift) to obtain a Fourier transformed correlation image, and then only an inverse Fourier transformation of the Fourier transformed correlation image must be performed to obtain the correlation image.

In accordance with a preferred embodiment of the afore-mentioned method, the step of performing the Fourier transformation of the first and second filtered images (in the above-described example the ridge and valley images) as well as the step of performing the inverse Fourier transformation of the Fourier transformed correlation image are carried out by using a Fast Fourier Transform algorithm. These are well-known numerical algorithms for very efficiently performing Fourier transformation and inverse Fourier transformation.

In some embodiments of the method according to the invention, the brightness of the two-dimensional correlation image is averaged at a specific radius over the entire circumference and wherein this averaging of the brightness over the entire circumference is performed at different radii to obtain a univariate correlation function. From this univariate correlation function the degree of stripedness in the two-dimensional image of the fixed cultured cells is obtained by determining the distance between two adjacent maxima in brightness or by determining the distance between a maximum and an adjacent minimum in brightness of the univariate correlation function, and by determining the ratio of the amplitudes in brightness of two adjacent maxima or the ratio of the amplitudes in brightness of a maximum and an adjacent minimum of the univariate correlation function.

This embodiment is advantageous in case the distribution of the striped structures in the two-dimensional image of the fixed cultured cells is isotropic (randomly oriented), since in this case at one specific radius in the correlation image the intensity is substantially homogeneously distributed over the circumference at this specific radius, so that through averaging no information is eliminated. The univariate correlation function is a convolution of the number of cells containing striped structures, the modulation amplitude of their stripes, and the homogeneity of their periodicity. In the univariate correlation function, the distance between two adjacent maxima or between a maximum and an adjacent minimum in brightness as well as the ratio of the amplitudes in brightness between two adjacent maxima or of the amplitudes in brightness of a maximum and an adjacent minimum are relevant features that report on the degree of stripedness in the two-dimensional image of the fixed cultured cells.

Some embodiments of the method according to the invention further comprises the step of performing a Fourier transformation of the two-dimensional correlation image to obtain a two-dimensional Fourier transformed correlation image. From this Fourier transformed correlation image the distance between two adjacent maxima in brightness is determined as a measure for the distance between the stripe-shaped structures in the two-dimensional image of the cultured cells. In addition, the angle under which the adjacent maxima in brightness are arranged is determined as representing the global orientation under which the periodic stripe-shaped structures are arranged in the two-dimensional image of the cultured cells.

This embodiment is advantageous in case the distribution of the striped structures is (globally) oriented in the two-dimensional image of the fixed cultured cells. In case of an oriented distribution of the striped structures in the two-dimensional image of the fixed cultured cells the Fourier transformed correlation image is more indicative of the striped structure than the afore-discussed univariate correlation function, since in the univariate correlation function orientation information is eliminated when averaging over the entire circumference at a specific radius. The Fourier transformation of the correlation image practically stands for a transformation from the x,y-coordinate system of the correlated image to a $k_x, k_y$-coordinate system (wave number) of the Fourier transformed correlation image. Accordingly, determining the wave number $k=\sqrt{k_x^2+k_y^2}=2\pi/\lambda$ allows determination of the wavelength of the periodic stripes from which the distance between the periodic stripes in the two-dimensional image of the fixed cultured cells can be calculated. The angle under which the patch of the periodic stripes is arranged can be determined from the Fourier transformed correlation image to be $$\varphi = \tan^{-1}\left(\frac{k_y}{k_x}\right).$$

Again, the step of performing a Fourier transformation of the two-dimensional cross-correlation image is preferably carried out using a well-known Fast Fourier Transform algorithm which has already been mentioned above.

Since it is not possible to predict in advance whether any stripe-shaped structures contained in the two-dimensional image of the fixed cultured cells are isotropic (randomly oriented) or (globally) oriented, in a preferred embodiment both the univariate correlation function and the Fourier transformed image of the correlation image are analyzed, and it is determined which one of them contains a more pronounced information as to the stripedness contained in the two-dimensional image of the fixed cultured cells.

As has already been mentioned above, while the method according to the invention is generally suitable to examine any types of cells for the presence of periodic structures contained in the cells, it is particularly suitable to determine whether myocytes or cardiomyocytes contain periodic sarcomere structures.

Accordingly, another aspect of the invention relates to a method for identifying a potential drug candidate substance for the treatment of muscle diseases or myocardium diseases associated with impairment of the sarcomere structures in the myocytes or cardiomyocytes. This method comprises the steps of:

providing a plurality of living myocytes or cardiomyocytes comprising sarcomere structures, adding a stressing substance to the plurality of living myocytes or cardiomyocytes causing the sarcomere structures to be destroyed or to at least be greatly reduced, after adding the stressing substance, adding a candidate substance to the plurality of myocytes or cardiomyocytes comprising the destroyed or at least greatly reduced sarcomere structures, culturing the myocytes or cardiomyocytes after having added the candidate substance, determining whether adding the candidate substance has resulted in sarcomere structures having developed in the cultured myocytes or cardiomyocytes again, in case adding the candidate substance has resulted in sarcomere structures having developed in the cultured myocytes or cardiomyocytes again, qualifying the candidate substance as a potential drug candidate substance.

Determining whether adding the candidate substance has resulted in sarcomere structures having developed in the cultured moycytes or cardiomyocytes again comprises using a method for examining cultured cells in accordance with any of the embodiments described above.

Another aspect of the invention relates to a method for identifying the ability of a potential drug candidate substance to have a protective effect against muscle diseases or myocardium diseases associated with impairment of sarcomere structures in myocytes or cardiomyocytes. The method comprises the steps of:

providing a plurality of living myocytes or cardiomyocytes comprising sarcomere structures, adding a candidate substance to the plurality of living myocytes or cardiomyocytes, after adding the candidate substance, adding a stressing substance to the plurality of living myocytes or cardiomyocytes causing the sarcomere structures to be destroyed or to at least be greatly reduced, culturing the myocytes or cardiomyocytes after having added the stressing substance, determining whether adding the stressing substance has resulted in the sarcomere structures having been destroyed or at least greatly reduced in the cultured myocytes or cardiomyocytes, in case adding the stressing substance has not resulted in the sarcomere structures having been destroyed or greatly reduced, qualifying the candidate substance as a potential drug candidate substance.

The step of determining whether adding the stressing substance has resulted in sarcomere structures having been destroyed or at least greatly reduced in the cultured myocytes or cardiomyocytes comprises using a method for examining cultured cells according to anyone of the embodiments described above.

This method is helpful in identifying potential drug candidate substances which may have a protective effect in that they either prevent or at least greatly reduce stress reactions of the myocytes or cardiomyocytes in case the myocytes or cardiomyocytes are exposed to substances (e.g. glucose and/or endothelin) which could otherwise lead to partial or total destruction of the sarcomere structures of the myocytes or cardiomyocytes. Such potential drug candidate substances may then be further evaluated for their potential to be developed to a drug which may form part of a protective or prophylactic treatment.

A further aspect of the invention relates to a method for determining the presence of sarcomere structures in living myocytes or cardiomyocytes obtained from living induced pluripotent stem cells. The method comprises the steps of:
  providing a plurality of living induced pluripotent stem cells,
  causing the living induced pluripotent stem cells to differentiate into living myocytes or cardiomyocytes,
  culturing the living myocytes of cardiomyocytes,
  determining whether the cultured myocytes or cardiomyocytes comprise sarcomere structures,
wherein the step of determining whether the cultured living myocytes or cardiomyocytes comprise sarcomere structures comprises using a method for examining cultured cells according to anyone of the embodiments described above.

This method allows for the assessment of a successful differentiation of living induced pluripotent stem cells into living myocytes or cardiomyocytes. The induced pluripotent stem cells may be obtained from dermal cells through re-programming and differentiation, for example. The structural integrity of the sarcomere contained in the so obtained myocytes or cardiomyocytes is indicative of the mature development of the myocytes or cardiomyocytes and, in the instant case, is then indicative of the successful differentiation of the pluripotent stem cells into myocytes or cardiomyocytes.

A further embodiment of this method comprises the additional steps of:
  before culturing the living myocytes or cardiomyocytes, adding a stressing substance to the living myocytes or cardiomyocytes causing the sarcomere structures to be destroyed or to at least be greatly reduced, and
  after having performed the method for examining cultured cells according to anyone of the embodiments described above, determining whether adding the stressing substance has resulted in the sarcomere structures having been destroyed or at least greatly reduced in the cultured myocytes or cardiomyocytes.

With this embodiment of the method it is possible to obtain information on the stress reaction of the myocytes or cardiomyocytes obtained in the afore-described manner. If the stress reaction of the myocytes or cardiomyocytes is a reaction one would expect from properly functioning myocytes or cardiomyocytes, then this embodiment of the method may from part of a diagnostic method. In such diagnostic method, for example, dermal cells may be harvested from a patient, re-programmed and differentiated into myocytes or cardiomyocytes. The so obtained myocytes or cardiomyocytes are then used to determine whether that patient may be prone to diseases of the muscles or the myocardium which are associated with impairment of the sarcomere structures upon exposure to specific substances (e.g. glucose and/or endothelin). Such method is not burdensome to the patient.

BRIEF DESCRIPTION OF THE DRAWINGS

Further advantageous aspects of the invention will become apparent from the following description of embodiments of the invention with the aid of the drawings in which:
FIG. 3 shows a schematic image of a fixed cardiomyocyte with globally oriented sarcomere structures;
FIG. 4 shows a correlation image generated through cross-correlation of the ridge and valley images derived from the image of the fixed cardiomyocyte of FIG. 3;
FIG. 5 shows the Fourier transformed correlation image of FIG. 4;
FIG. 6 shows a schematic image of a fixed cardiomyocyte with randomly oriented (isotropic) sarcomere structures;
FIG. 7 shows the correlation image generated through cross-correlation of the ridge and valley images derived from the image of the fixed cardiomyocyte of FIG. 6;
FIG. 8 shows the Fourier transformed correlation image of FIG. 7;
FIG. 9 shows a schematic image of a fixed cardiomyocyte with no sarcomere structures;
FIG. 10 shows the correlation image generated through cross-correlation of the ridge and valley images derived from the image of the fixed cardiomyocyte of FIG. 9;
FIG. 11 shows the Fourier transformed correlation image of FIG. 10.

Figure 1:
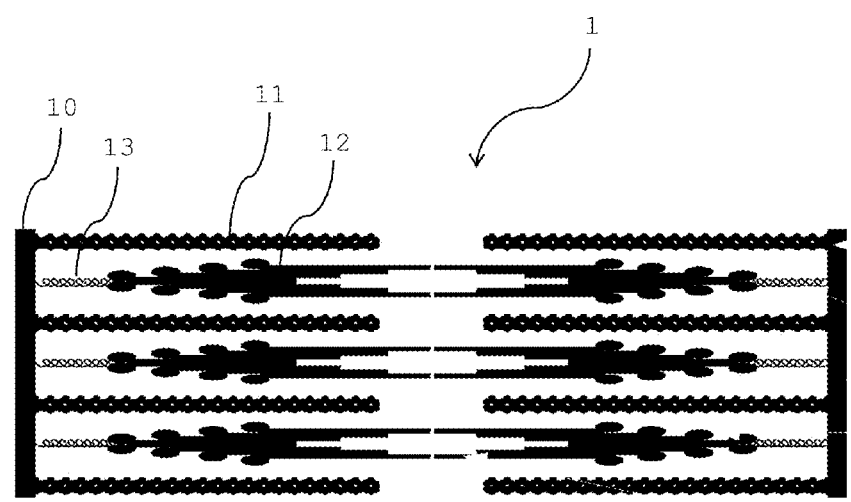
FIG. 1 shows a schematic view of a sarcomere in the relaxed state.
Figure 2:
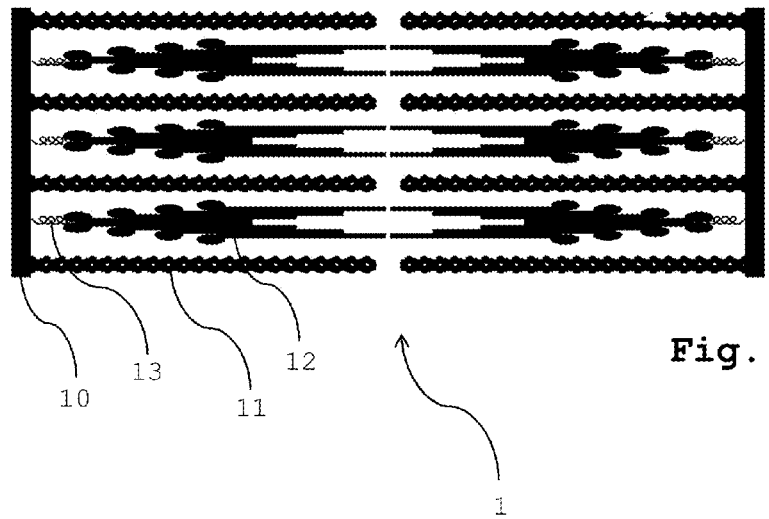
FIG. 2 shows the sarcomere of FIG. 1 in the contracted state.

The sarcomere 1 and its general structure shown in FIG. 1 and FIG. 2 have already been explained above so that this explanation is not reiterated here. An image 2 of a fixed myocyte or cardiomyocyte shows periodic sarcomere structures 20 which are arranged with a global orientation as this is shown in the schematic two-dimensional image 2 of the cardiomyocyte shown in FIG. 3. The direction 21 of global orientation of the periodic sarcomere structures 1 in the image 2 of the cardiomyocyte is indicated by a straight line which is not part of the image 2 of the cardiomyocyte.

The two-dimensional image 2 of the cardiomyocyte shown in FIG. 3 is then subjected to a ridge-valley filtering operation. A two-dimensional ridge image is thereby generated showing in bright any striped-shaped sarcomere structures contained in the image 2 of the cardiomyocyte. Any structures other than stripe-shaped sarcomere structures are suppressed by the ridge filtering operation. Also, a valley-image is generated showing in bright any stripe-shaped structures arranged between the stripe-shaped structures of the ridge image, whereas structures other than these are suppressed in by the valley filtering operation. Ridge image and valley image are not shown here as they are only intermediate images which are not analyzed per se (a ridge image is shown, for example, in FIG. 12). They are anti-correlated by definition, and their purpose is to enhance stripe-shaped structures contained in an image while suppressing structures other than stripe-shaped structures, so that periodic structures contained in the image 2 of the cardiomyocyte lead to more pronounced features indicating the presence of such periodic structures in the resulting correlation image.

The ridge and valley images are cross-correlated. As mentioned already, cross-correlation of the ridge and valley images is performed in order to make sure that any information on stripe-shaped structures contained in either of the ridge and valley images is considered during generation of the correlation image. Alternatively, it is generally also possible to only auto-correlate the ridge image, for example. However, auto-correlation of the ridge image only means that any information on stripe-shaped structures contained in the valley image which is not contained in the ridge image (due to having been suppressed there) is not considered when generating the correlation image.

Cross-correlation of the ridge and valley images means that a convolution of the ridge and valley images must be performed, as this has been explained above. This convolution is a mathematical operation involving a large amount of computational work, as has already been explained above. However, this large amount of computational work can be significantly reduced by performing Fourier transformations of the ridge image and of the valley image into Fourier space, and by multiplying the Fourier transformed ridge image with the Fourier transformed valley image (more precisely: the brightness values of the pixels of the Fourier transformed ridge image and the Fourier transformed valley image), since the convolution of the ridge and valley images corresponds to a multiplication of the Fourier transformed ridge image and the Fourier transformed valley image in Fourier space. This multiplication of the Fourier transformed ridge image with the Fourier transformed valley images results in a Fourier transformed correlation image, of which an inverse Fourier transformation must be performed to obtain the correlation image shown in FIG. 4. Alternatively, as mentioned, this correlation image can also be obtained through convolution of the (not Fourier transformed) ridge and valley images.

The correlation image 3 shown in FIG. 4 (generated through cross-correlation of the ridge and valley images, as outlined above) shows a periodic arrangement of maxima 30 and minima 31 in brightness. This periodic arrangement of the maxima 30 and minima 31 in brightness is generally globally aligned in the same direction 32 (indicated by a straight line in FIG. 4 which is not part of the correlation image) as are the periodic sarcomere structures 20 in the image 2 of the cardiomyocyte (see FIG. 3). The amplitudes in brightness depend on the coherence of the periodic sarcomere structures 1 in the image 2 of the fixed cardiomyocyte (FIG. 3).

FIG. 5 shows a Fourier transformed correlation image 4 which is a Fourier transformation of the correlation image 3 shown in FIG. 4. This Fourier transformation corresponds to a transformation from the x,y-space in the correlation image 3 to the $k_x,k_y$-space in the Fourier transformed correlation image 4. In this Fourier transformed correlation image, the modulation amplitude (the ratio of two adjacently arranged maxima in brightness or the ratio of a maximum in brightness and an adjacent minimum), the frequency, and the direction report on the degree of stripedness contained in the image 2 of the cardiomyocyte. As can be seen, an extended region of parallel stripes (sarcomere structures 20) in the image 2 of the cardiomyocyte (see FIG. 3) is transformed into a local maximum 40 located at a distance $k=\sqrt{k_x^2+k_y^2}=2\pi/\lambda$ from the origin (indicated in FIG. 5 through the black line which is not part of the Fourier transformed image 4, with $\lambda$ being the "wavelength" of the periodic stripes contained in the image 2), and at an angle $$\varphi = \tan^{-1}\left(\frac{k_y}{k_x}\right).$$

The Fourier transformed image 4 contains pronounced features and is therefore particularly suitable for the analysis of examined fixed cells which contain globally aligned striped structures.

FIG. 6 shows an image 2 of a fixed myocyte or cardiomyocyte also containing periodic sarcomere structures 20, however, these periodic sarcomere structures 20 are not arranged with a global orientation but rather are randomly oriented (isotropic) at different directions. As a consequence, the correlation image 3 shown in FIG. 7 generated through cross-correlation of the ridge and valley images shows maxima 30 and minima 31 in brightness, however, due to the random orientation (or isotropic orientation) of the periodic sarcomere structures in all directions in the image 2 the maxima 30 and minima 31 form rings in the correlation image with decreasing amplitude in brightness (these rings being indicative of the distribution of the structures in all directions). The amplitude in brightness depends on the number of "patches" of periodic sarcomere structures, and the width of the rings depends on the width and the jitter of the individual periodic sarcomere structures. Accordingly, the Fourier transformed correlation image 4 shown in FIG. 8 shows no preferred direction but the maximum 40 is still located at the afore-described distance in the $k_x,k_y$-space.

FIG. 9 shows an image 2 of a fixed myocyte or cardiomyocyte which does not show any periodic sarcomere structures at all. Accordingly, the correlation image 3 does not show any periodic structures of maxima and minima (see FIG. 10), either, and this holds for the Fourier transformed correlation image 4, too (see FIG. 11).

Figure 12:
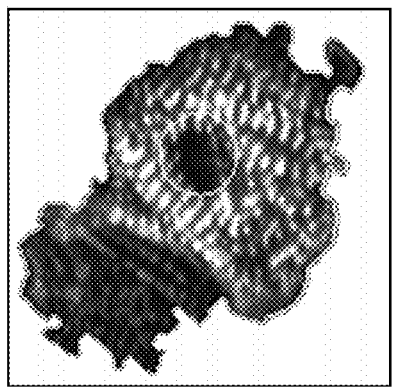
FIG. 12 shows an Actinin stain image of a real cardiomyocyte with globally oriented sarcomere structures.
Figure 13:
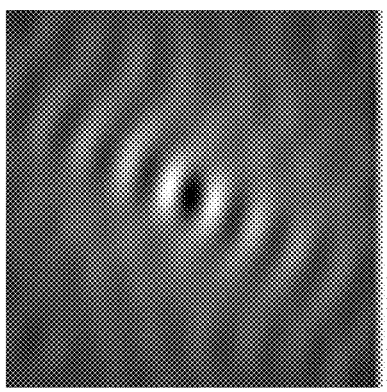
FIG. 13 shows the correlation image generated through cross-correlation of the ridge and valley images derived from the image of the real cardiomyocyte of FIG. 12.
Figure 14:
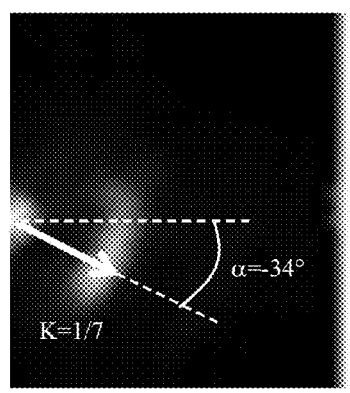
FIG. 14 shows the Fourier transformed correlation image of FIG. 13.
Figure 15:
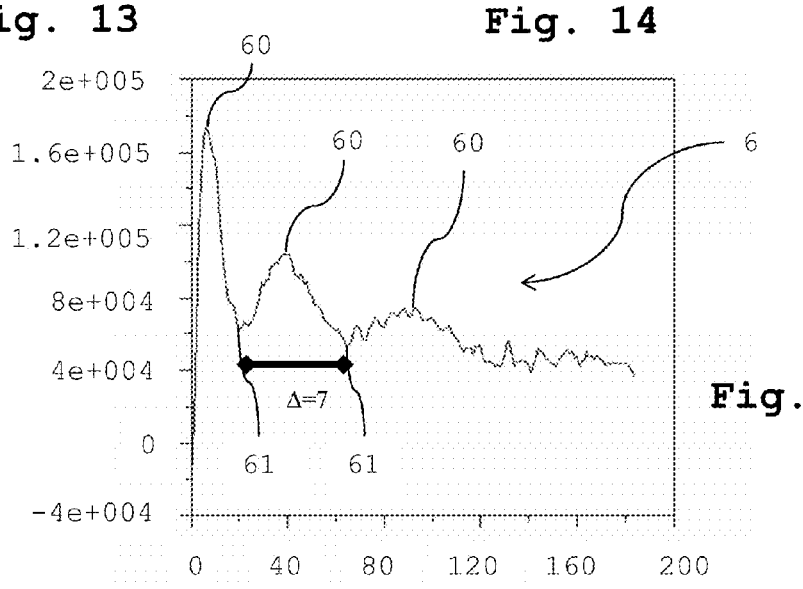
FIG. 15 shows the univariate correlation function generated from the correlation image of FIG. 13.

FIG. 12 shows a ridge image 5 of a real fixed cardiomyocyte containing sarcomere structures which appear bright in FIG. 12. In FIG. 13 a real correlated image 3 generated through cross-correlation of the ridge image 5 of the cardiomyocyte (FIG. 12) and the valley image of the cardiomyocyte (not shown) is shown, and FIG. 14 shows the corresponding Fourier transformed correlated image 4 from which the value K can be determined as is indicated by the arrow (this value K being representative of the "wavelength" of the sarcomere structures contained in the image of the cardiomyocyte; in the afore-mentioned examples this value K has been designated k) and the angle α of the global direction of the orientation of the sarcomere structure in the image of the cardiomyocyte (this angle α has been designated φ in the afore-mentioned examples). Since the Actinin stain image 5 shows the sarcomere structure, it is evident that the direction of the orientation in FIG. 14 is correct (this direction of orientation can also be recognized when glancing at the correlation image 3 in FIG. 13). In FIG. 15 a univariate correlation function 6 is shown, and this univariate correlation function 6 has been obtained by averaging the brightness of the correlation image at a specific radius over the entire circumference, and then reiterating this averaging for different radii. Since at some specific radii there is an enhanced brightness contained in the correlation image 3 while at other specific radii there is essentially no or only low brightness, the univariate correlation function exhibits maxima 60 and minima 61 in brightness. However, due to the averaging being performed at a specific radius over the entire circumference, any information on the orientation of the periodic sarcomere structures is not contained in the correlation function 6. The distance between two adjacent maxima 60 or minima 61 in brightness of the univariate correlation function 6, the ratio of the amplitudes in brightness of two adjacent maxima 60 or the ratio of the amplitudes of a maximum 60 and an adjacent minimum 61 and the homogeneity of the periodicity of the maxima 60 and minima 61 report on the degree of stripedness contained in the image of the cardiomyocyte.

As has already been mentioned above, in case of randomly distributed periodic sarcomere structures in the image of the fixed cardiomyocyte the correlation function 6 is more representative and contains more pronounced features since the averaging process in this case does not remove much information since there is practically no preferred orientation of the periodic structures. In case of globally oriented periodic sarcomere structures in the image of the fixed cardiomyocyte the Fourier transformed image 4 of the correlation function is more representative and contains more pronounced features, since the averaging performed to obtain the correlation function 6 then removes information as to preferred directions of orientation. Since it is not possible to predict in advance which analysis is more promising both the analysis of the correlation function 6 and the analysis of the Fourier transformed correlation image 4 are performed, and from the results of both analyses it can then be determined which one is the more representative analysis.

Figure 16:
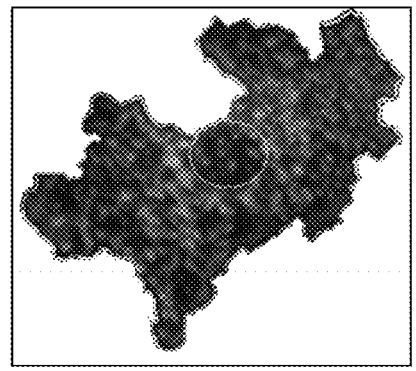
FIG. 16 shows an Actinin stain image of a real cardiomyocyte with no sarcomere structures.
Figure 17:
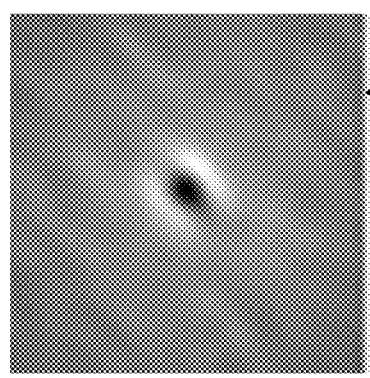
FIG. 17 shows the correlation image generated through cross-correlation of the ridge and valley images derived from the cardiomyocyte image of FIG. 16.
Figure 18:
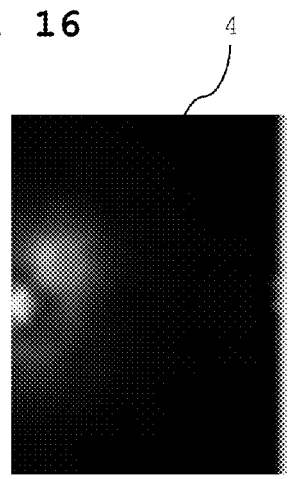
FIG. 18 shows the Fourier transformed correlation image of FIG. 17.
Figure 19:
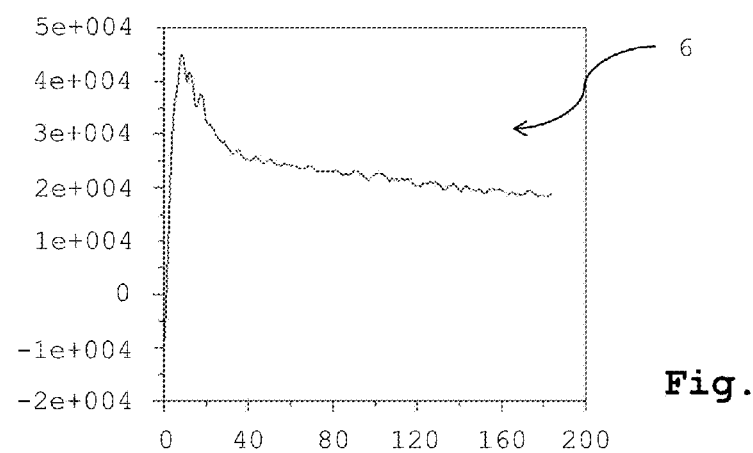
FIG. 19 shows the univariate correlation function generated from the correlation image of FIG. 17.

FIG. 16 shows an Actinin stain image 5 of a real fixed cell containing no periodic structures. Accordingly, the correlation image 3 shown in FIG. 17, the corresponding Fourier transformed correlated image 4 shown in FIG. 18, and the univariate correlation function 6 shown in FIG. 19 do not show any specific features that could be used for an analysis, so that the conclusion is that there are no periodic structures contained in the image of the fixed cell.

As has been explained already, the afore-described embodiments of the method of examining cultured cells has a particularly advantageous field of application in the detection of potential drug candidate substances for the treatment of muscle diseases or myocardium diseases which are associated with an impairment of the sarcomere structures in the myocytes of cardiomyocytes, since the living myocytes or cardiomyocytes comprising the sarcomere structures can first be stressed by adding one or more substances like glucose or endothelin to the living myocytes or cardiomyocytes to destroy or at least greatly reduce the sarcomere structures and then a potential drug candidate substance can be added. Thereafter, the myocytes or cardiomyocytes are cultured again, and these cultured cells are then fixed and analyzed in accordance with the afore-described embodiments.

EXAMPLE

Human cardiomyocytes are seeded at 35000/well in Becton Dickinson Falcon thin bottom 96 well micro-plates coated with gelatin or fibronectin. The cardiomyocytes are allowed to attach for 2 days. Remove medium and add new medium containing 10 mM glucose and 10 nM endothelin for 2 days. Fixation is then performed with 4% paraformaldehyde for fifteen minutes, then permeabilization with 0.1% Tween20 for 15 minutes. Thereafter, staining is performed. The following antibodies are used: anti human alpha Actinin primary AB9465 clone EA53-monoclonal diluted 1/120 (available from Abcam plc 330, Cambridge, United Kingdom), anti-human Troponin T primary AB45932 polyclonal in Rabbit diluted 1/120 (available from Abcam plc, Cambridge, United Kingdom), secondary AB goat anti mouse AlexaFluor488 A-11029 diluted 1/200 (available from Life Technologies, Carlsbad, Calif., United States of America), secondary AB donkey anti rabbit AlexaFluor647 A-11029 diluted 1/200 (available from Life Technologies, Carlsbad, Calif., United States of America). All staining steps are performed at room temperature for 30 minutes followed by 3 washes with phosphate buffered saline (PBS). Antibody staining of Actinin produces extended periodic stripe patterns in mature myocytes but no or unstructured staining in pre-mature or compromised cells.

The images are acquired on the Opera™ QEHS High-Content Screening system (commercially available from PerkinElmer Cellular Technologies). This system comprises a multi-color automated spinning disk confocal microscope for multi-well plates. Excitation occurs through a 20× NA 0.7 water immersion objective by 3 lasers at 640 nm, 488 nm, and 405 nm. For each marker channel one image is recorded subsequently with an exposure time of 2 s, 1 s, and 0.8 s, for the Troponin C marker (red channel), the Actinin marker (green channel) and the Hoechst DNA marker (blue channel), respectively. The emission filters are chosen to trade off maximum detection efficiency and minimum cross-talk.

Image analysis is then performed using the proprietary script language Acapella™ (PerkinElmer Cellular Technologies) included in the Opera™ QEHS High-Content Screening system. After user-defined setting of adjustment parameters the analysis is run without human intervention in the same way for all images.

The two cytoskeletal marker channels Actinin and Troponin C do not show the stripe pattern to the same extent and contrast. The more pronounced Actinin signal was chosen for quantification of the stripe pattern. The Actinin image was filtered using the proprietary ridge and valley filters from the "SER( )" function ("Spots, Edges and Ridges") in the Acapella™ texture feature extraction library (PerkinElmer) to derive the ridge image and the valley image) which enhance bright and dark lines. These ridge and valley images are then correlated by Fourier transforming the ridge and valley images using the Fast Fourier Transform algorithm, multiplying the Fourier transformed ridge and valley images to generate a Fourier transformed correlation image, and then performing an inverse Fourier transformation to generate the correlation image. The correlation image, the Fourier transformed correlation image, and the univariate correlation function are generated and are analyzed as this has been described above.

Embodiments of the invention have been described above with the aid of the drawings and in the Example. However, the invention is not limited to these embodiments, but rather various modifications and changes are conceivable without departing from the teaching of the present invention. Therefore, the scope of protection is not limited by the embodiments but rather is defined by the appended claims.

The invention claimed is:

1. A method for examining a plurality of cultured cells for the presence of periodic structures of at least one target component contained in the cultured cells, the method comprising the steps of:
   providing a plurality of cultured cells to be examined,
   fixing the cultured cells to be examined while maintaining any structures of the at least one target component contained in the cultured cells, staining the at least one target component contained in the fixed cultured cells using a first staining agent binding to the at least one target component and capable of emitting light of a first wavelength upon stimulation, stimulating the first staining agent causing it to emit light of the first wavelength, taking a two-dimensional image of the fixed cultured cells with the first staining agent emitting light of the first wavelength, deriving from this two-dimensional image of the fixed cultured cells a two-dimensional first filtered image showing in bright only those portions containing the at least one target component to which the first staining agent has bound, auto-correlating the first filtered image, or cross-correlating the first filtered image with a second two-dimensional filtered image derived from the two-dimensional image of the fixed cultured cells and showing in bright only those portions other than the ones containing the at least one target component to which the first staining agent has bound, to obtain a two-dimensional correlation image, and determining the presence or absence of periodic structures of the at least one target component contained in the fixed cultured cells by determining whether there are periodic structures of maxima and minima in brightness in the correlation image.

2. A method according to claim 1, wherein the step of deriving the two-dimensional first and second filtered images comprises performing a ridge-valley filtering of the two-dimensional image of the fixed cultured cells, to generate a two-dimensional ridge image in which stripe-shaped structures of the at least one target component to which the first staining agent has bound are enhanced in brightness and in which any structures other than stripe-shaped structures of the at least one target component to which the first staining agent has bound are attenuated in brightness, said ridge image forming the first filtered image, and to generate a two-dimensional valley image in which stripe-shaped structures arranged between the stripe-shaped structures of the target component to which the first staining agent has bound are enhanced in brightness and in which structures other than stripe-shaped structures arranged between the stripe-shaped structures to which the first staining agent has bound are attenuated in brightness, said valley image forming the second filtered image, and wherein the ridge image and the valley image are cross-correlated to form the correlation image.

3. A method according to claim 1, wherein the correlation image is generated by:

performing a Fourier transformation of the first filtered image to obtain a two-dimensional Fourier transformed first filtered image and multiplying the Fourier transformed first filtered image with itself to obtain a two-dimensional Fourier transformed correlation image, or performing a Fourier transformation of the first filtered image and performing a Fourier transformation of the second filtered image to obtain a two-dimensional Fourier transformed second filtered image and multiplying the Fourier transformed first filtered image and the Fourier transformed second filtered image to obtain a two-dimensional Fourier transformed correlation image, performing an inverse Fourier transformation of the Fourier transformed correlation image to obtain the two-dimensional correlation image.

4. A method according to claim 3, wherein the step of performing the Fourier transformation of the first and second filtered images as well as the step of performing the inverse Fourier transformation of the Fourier transformed correlation image are carried out by using a Fast Fourier Transform algorithm.

5. A method according to claim 4, wherein the brightness of the two-dimensional correlation image is averaged at a specific radius over the entire circumference and wherein this averaging of the brightness over the entire circumference is performed at different radii to obtain a univariate correlation function, and wherein from this univariate correlation function the degree of stripedness in the two-dimensional image of the fixed cultured cells is obtained by determining the distance between two adjacent maxima in brightness or by determining the distance between a maximum and an adjacent minimum in brightness of the univariate correlation function, and by determining the ratio of the amplitudes in brightness of two adjacent maxima or the ratio of the amplitudes in brightness of a maximum and an adjacent minimum of the univariate correlation function.

6. A method according to claim 5, further comprising the step of performing a Fourier transformation of the two-dimensional correlation image to obtain a two-dimensional Fourier transformed correlation image, wherein from this Fourier transformed correlation image the distance (k,K) between two adjacent maxima in brightness is determined as a measure for the distance between the stripe-shaped structures in the two-dimensional image of the cultured cells, and wherein further the angle ($\varphi,\alpha$) under which the adjacent maxima in brightness are arranged is determined as representing the global orientation under which the periodic stripe-shaped structures are arranged in the two-dimensional image of the cultured cells.

7. A method according to claim 6, wherein the step of performing a Fourier transformation of the two-dimensional correlation image is carried out using a Fast Fourier transform algorithm.

8. A method for identifying a potential drug candidate substance for the treatment of muscle diseases or myocardium diseases associated with impairment of sarcomere structures in myocytes or cardiomyocytes, the method comprising the steps of:

providing a plurality of living myocytes or cardiomyocytes comprising sarcomere structures, adding a stressing substance to the plurality of living myocytes or cardiomyocytes causing the sarcomere structures to be destroyed or to at least be greatly reduced, after adding the stressing substance, adding a candidate substance to the plurality of myocytes or cardiomyocytes comprising the destroyed or at least greatly reduced sarcomere structures, culturing the myocytes or cardiomyocytes after having added the candidate substance, determining whether adding the candidate substance has resulted in sarcomere structures having developed in the cultured myocytes or cardiomyocytes again, in case adding the candidate substance has resulted in sarcomere structures having developed in the cultured myocytes or cardiomyocytes again, qualifying the candidate substance as a potential drug candidate substance, wherein the step of determining whether adding the candidate substance has resulted in sarcomere structures having developed in the cultured moycytes or cardio-myocytes again comprises using a method according to claim 1.

9. A method for identifying the ability of a potential drug candidate substance to have a protective effect against muscle diseases or myocardium diseases associated with impairment of sarcomere structures in myocytes or cardio-myocytes, the method comprising the steps of:
- providing a plurality of living myocytes or cardiomyocytes comprising sarcomere structures,
- adding a candidate substance to the plurality of living myocytes or cardiomyocytes,
- after adding the candidate substance, adding a stressing substance to the plurality of living myocytes or cardio-myocytes causing the sarcomere structures to be destroyed or to at least be greatly reduced,
- culturing the myocytes or cardiomyocytes after having added the stressing substance,
- determining whether adding the stressing substance has resulted in the sarcomere structures having been destroyed or at least greatly reduced in the cultured myocytes or cardiomyocytes,
- in case adding the stressing substance has not resulted in the sarcomere structures having been destroyed or greatly reduced, qualifying the candidate substance as a potential drug candidate sub stance,
- wherein the step of determining whether adding the substance has resulted in sarcomere structures having been destroyed or at least greatly reduced in the cultured myocytes or cardio-myocytes comprises using a method according to claim 1.

10. A method for determining the presence of sarcomere structures in living myocytes or cardiomyocytes obtained from living induced pluripotent stem cells, the method comprising the steps of:
- providing a plurality of living induced pluripotent stem cells,
- causing the living induced pluripotent stem cells to differentiate into living myocytes or cardiomyocytes,
- culturing the living myocytes of cardiomyocytes,
- determining whether the cultured myocytes or cardio-myocytes comprise sarcomere structures,
- wherein the step of determining whether the cultured living myocytes or cardiomyocytes comprise sarcomere structures comprises using a method according to claim 1.

11. A method according to claim 10, further comprising the steps of:
- before culturing the living myocytes or cardiomyocytes, adding a stressing substance to the living myocytes or cardiomyocytes causing the sarcomere structures to be destroyed or to at least be greatly reduced, and
- after having performed the method according to claim 1, determining whether adding the stressing substance has resulted in the sarcomere structures having been destroyed or at least greatly reduced in the cultured myocytes or cardiomyocytes.

* * * * *